(12) United States Patent
Sudakov et al.

(10) Patent No.: US 6,923,756 B2
(45) Date of Patent: Aug. 2, 2005

(54) MULTIFUNCTIONAL MEDICAL TOOL

(75) Inventors: Boris Sudakov, Salant St. 47/1, 49530 Petach Tikva (IL); Menachem Hoover, Zichron Yaakov (IL)

(73) Assignee: Boris Sudakov, Rehovot (IL)

( * ) Notice: Subject to any disclaimer, the term of this patent is extended or adjusted under 35 U.S.C. 154(b) by 96 days.

(21) Appl. No.: 10/296,974

(22) PCT Filed: Jun. 3, 2001

(86) PCT No.: PCT/IL01/00512

§ 371 (c)(1),
(2), (4) Date: Dec. 2, 2002

(87) PCT Pub. No.: WO01/93742

PCT Pub. Date: Dec. 13, 2001

(65) Prior Publication Data

US 2004/0015051 A1 Jan. 22, 2004

(30) Foreign Application Priority Data

Jun. 5, 2000 (IL) .................................. 136571

(51) Int. Cl.⁷ .............................................. A61B 1/00
(52) U.S. Cl. ........................ 600/101; 600/104; 600/114
(58) Field of Search ................................. 600/101, 104, 600/114, 156, 158

(56) References Cited

U.S. PATENT DOCUMENTS

| | | | |
|---|---|---|---|
| 5,158,563 A | 10/1992 | Cosman | 606/140 |
| 5,186,714 A | 2/1993 | Boudreault et al. | 604/21 |
| 5,464,412 A | 11/1995 | Budding | 606/140 |
| 5,755,713 A | 5/1998 | Bilof et al. | 606/1 |
| 5,921,917 A | 7/1999 | Barthel et al. | 600/120 |
| 5,935,097 A | 8/1999 | Metsch et al. | 604/27 |
| 6,083,151 A | 7/2000 | Renner et al. | 600/114 |
| 6,129,661 A | 10/2000 | Iafrati et al. | 600/121 |
| 6,165,123 A | 12/2000 | Thompson | 600/152 |

*Primary Examiner*—Beverly M. Flanagan
(74) *Attorney, Agent, or Firm*—Blank Rome LLP

(57) ABSTRACT

A multifunctional medical tool for use in proctologic applications, during which a surgeon has to manipulate a surgical instrument, brought within the anal canal. The tool comprises a pistol-grip portion (10) to carry the surgical instrument, an endoscopic means (30') for insertion within the anal canal and surgical instrument (56), which can be brought in the anal canal through the endoscopic means (30'). The tool can be used for endoscopic examination or for various invasive proctologic treatments within the anal canal, rectum or distal colon.

16 Claims, 11 Drawing Sheets

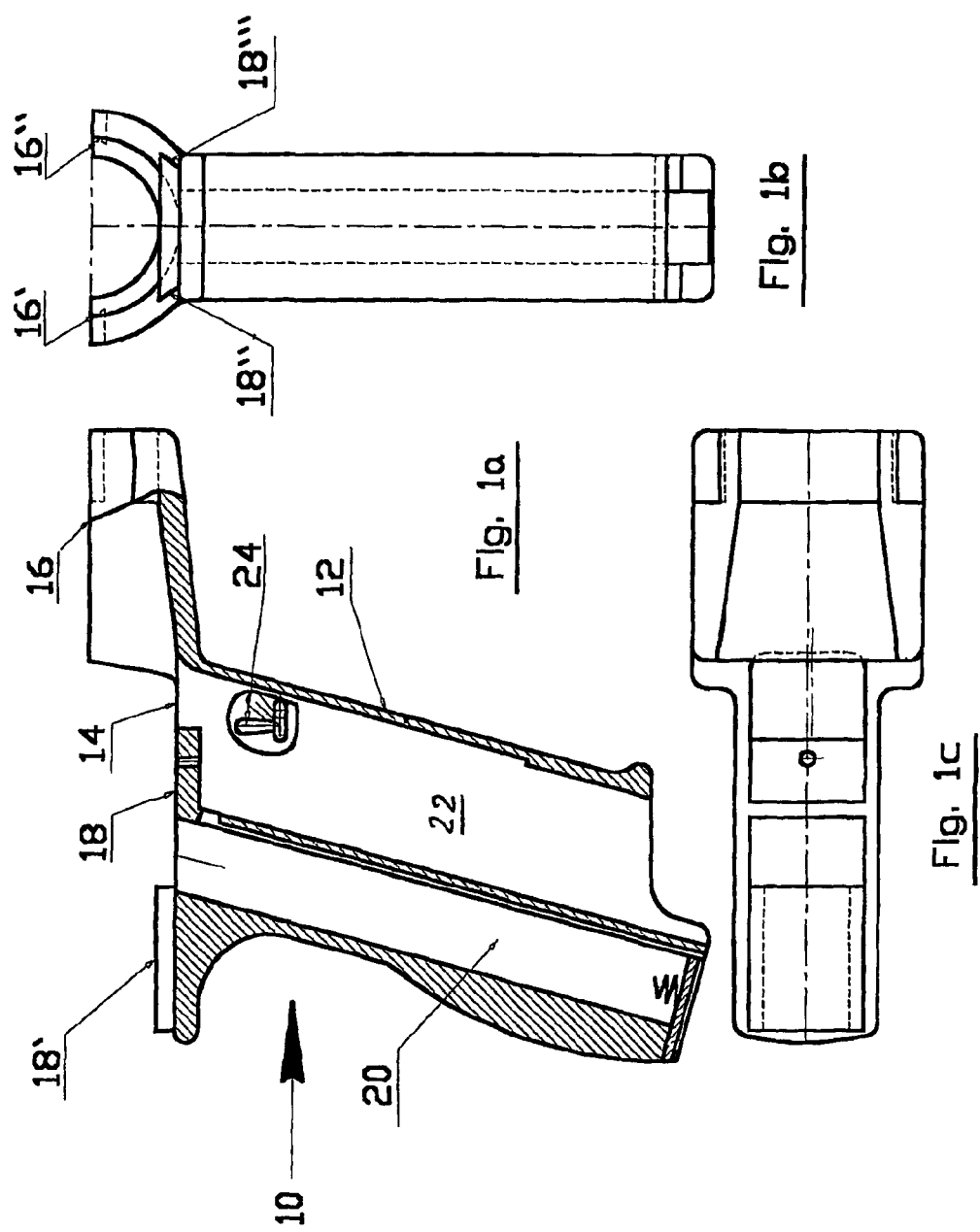

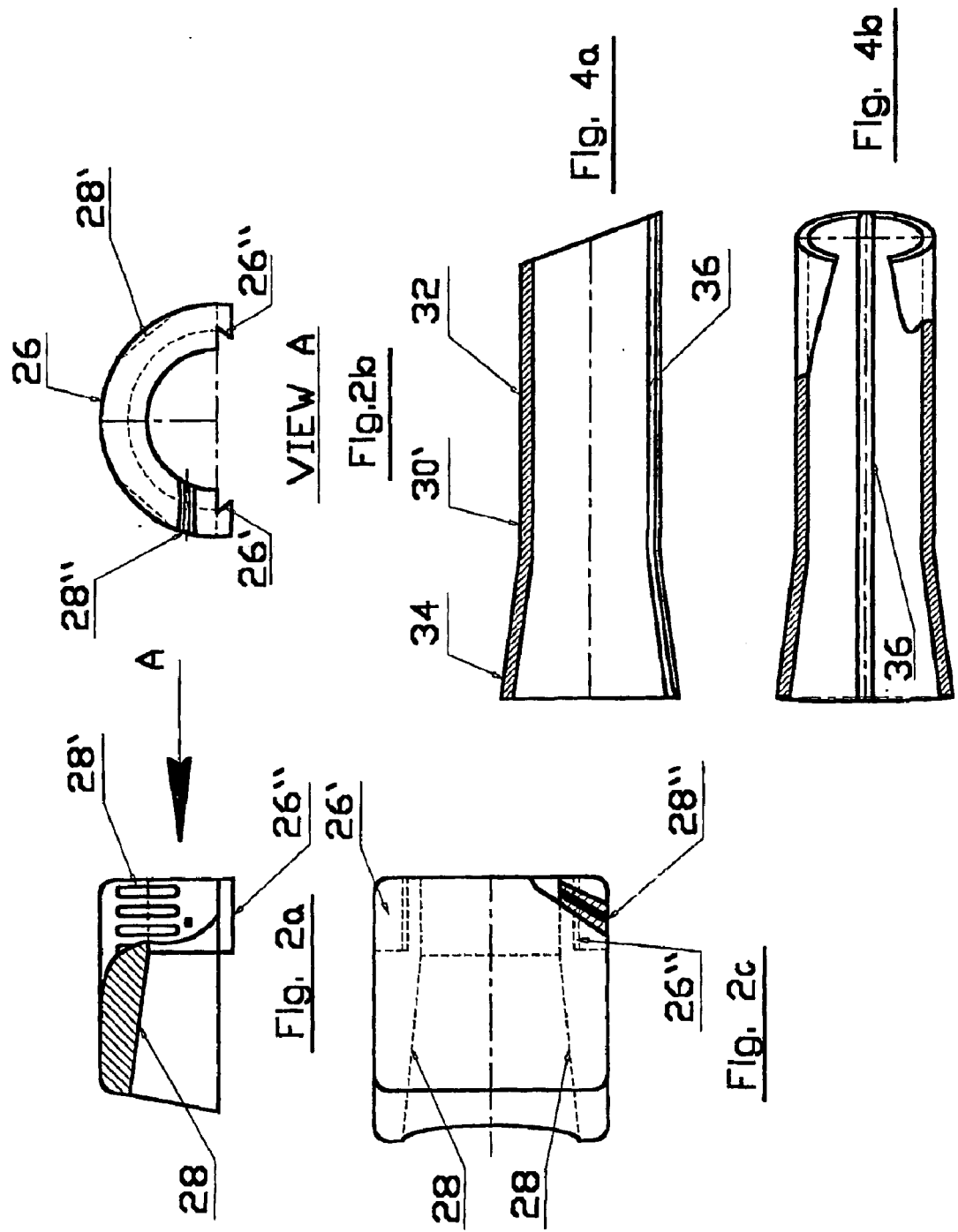

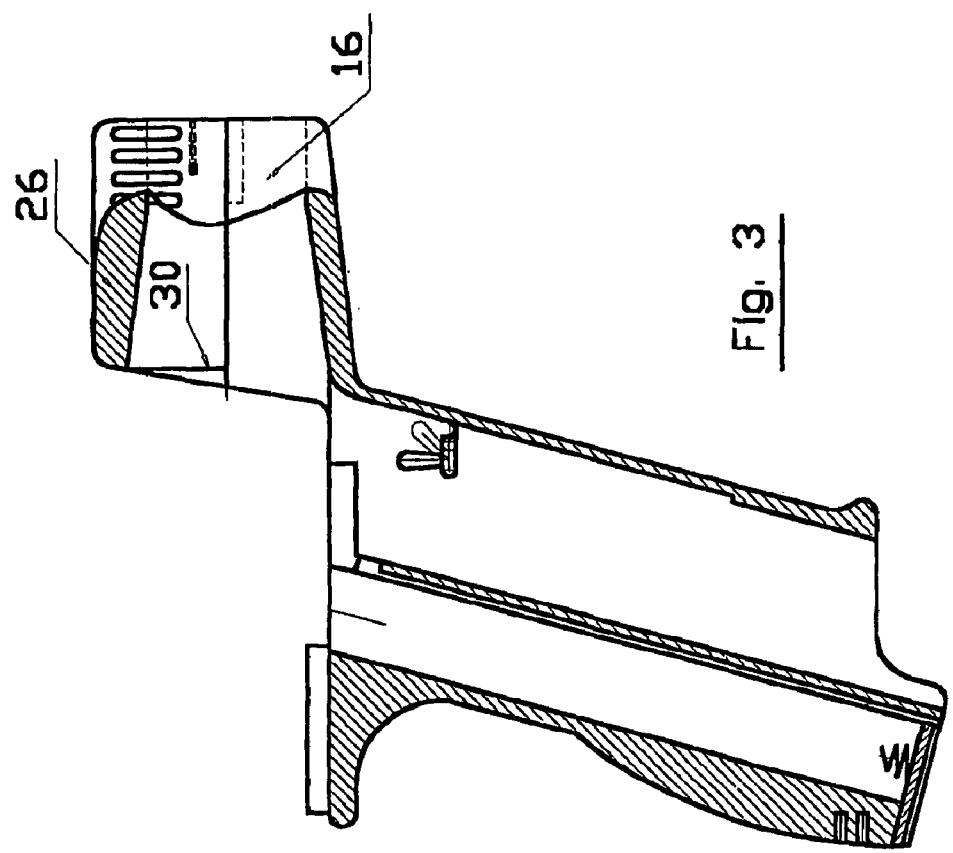

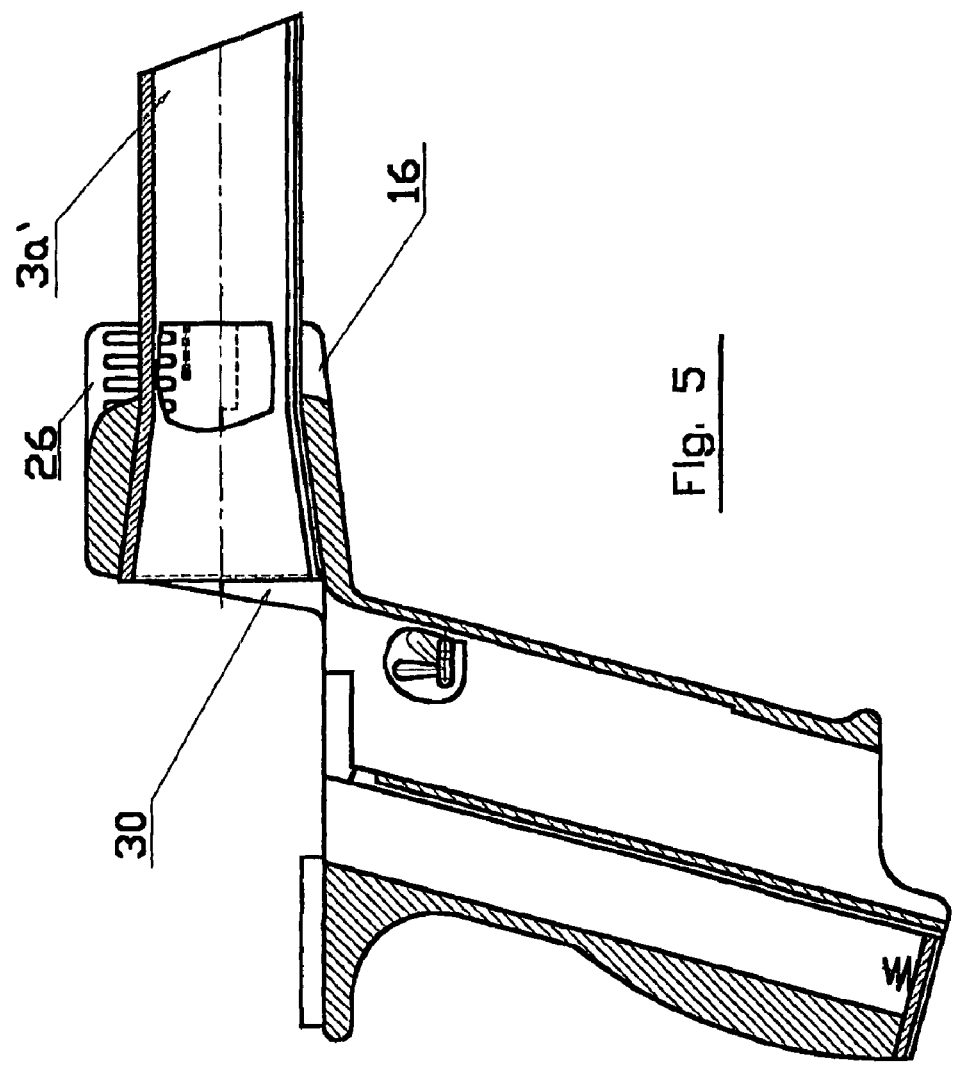

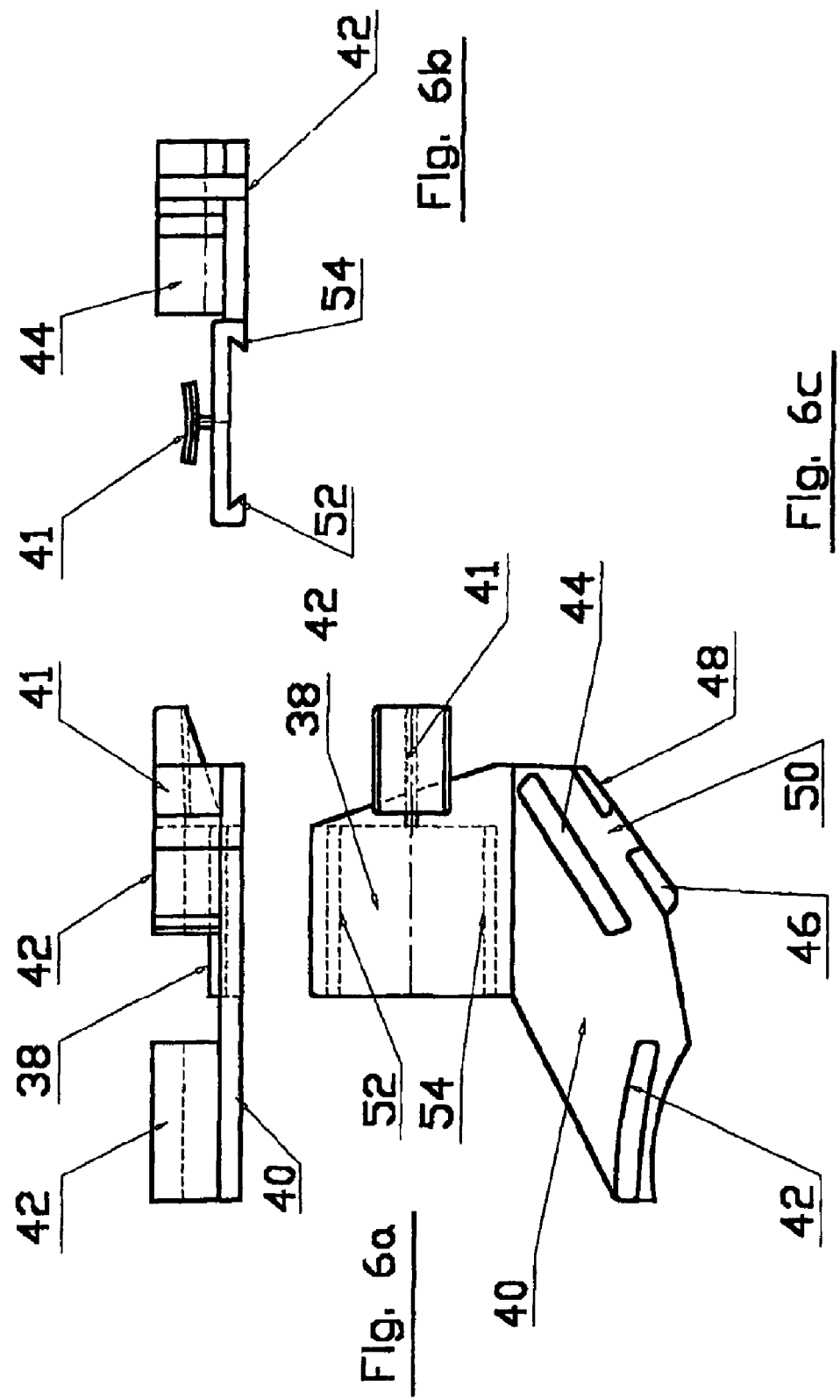

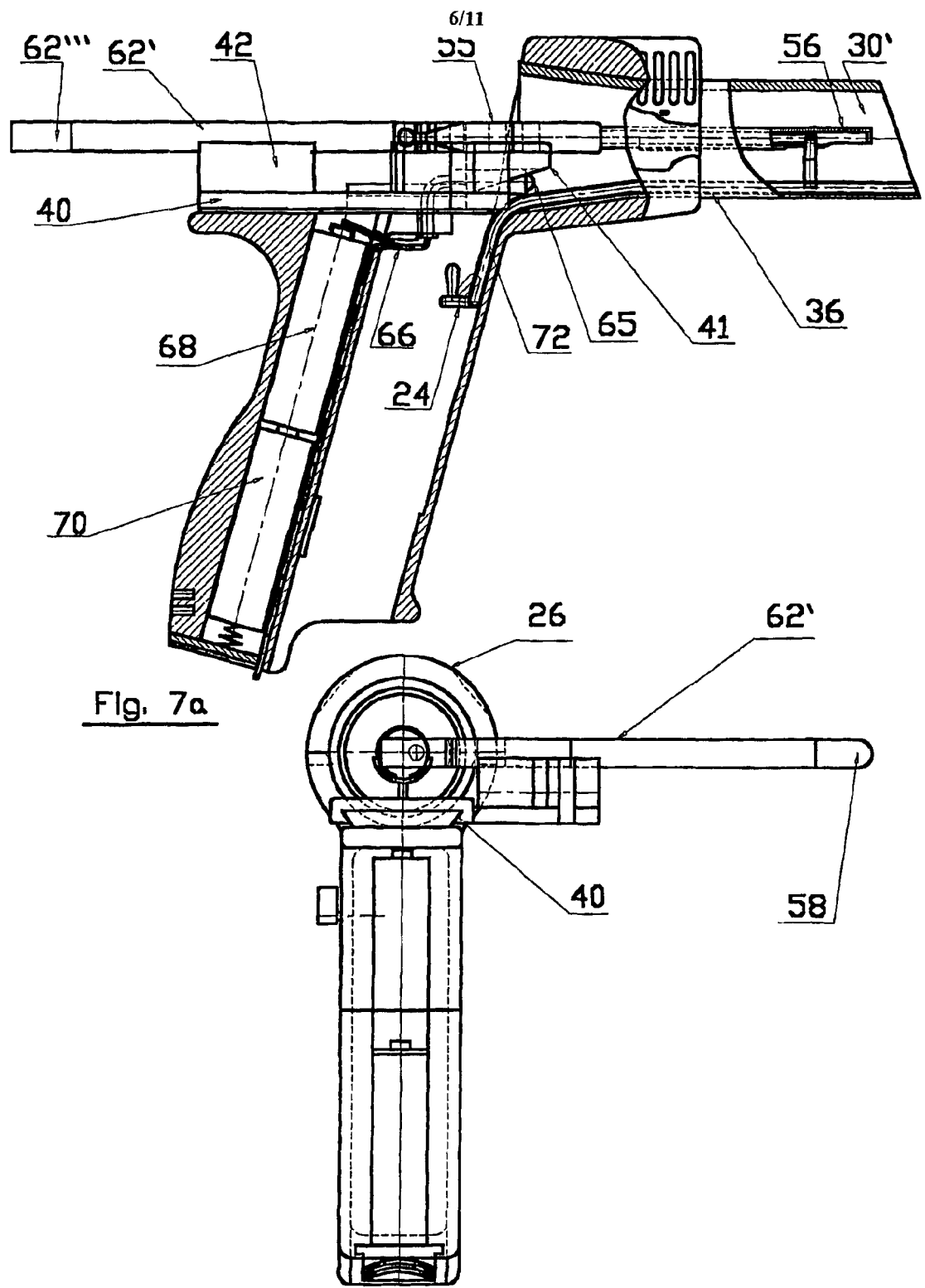

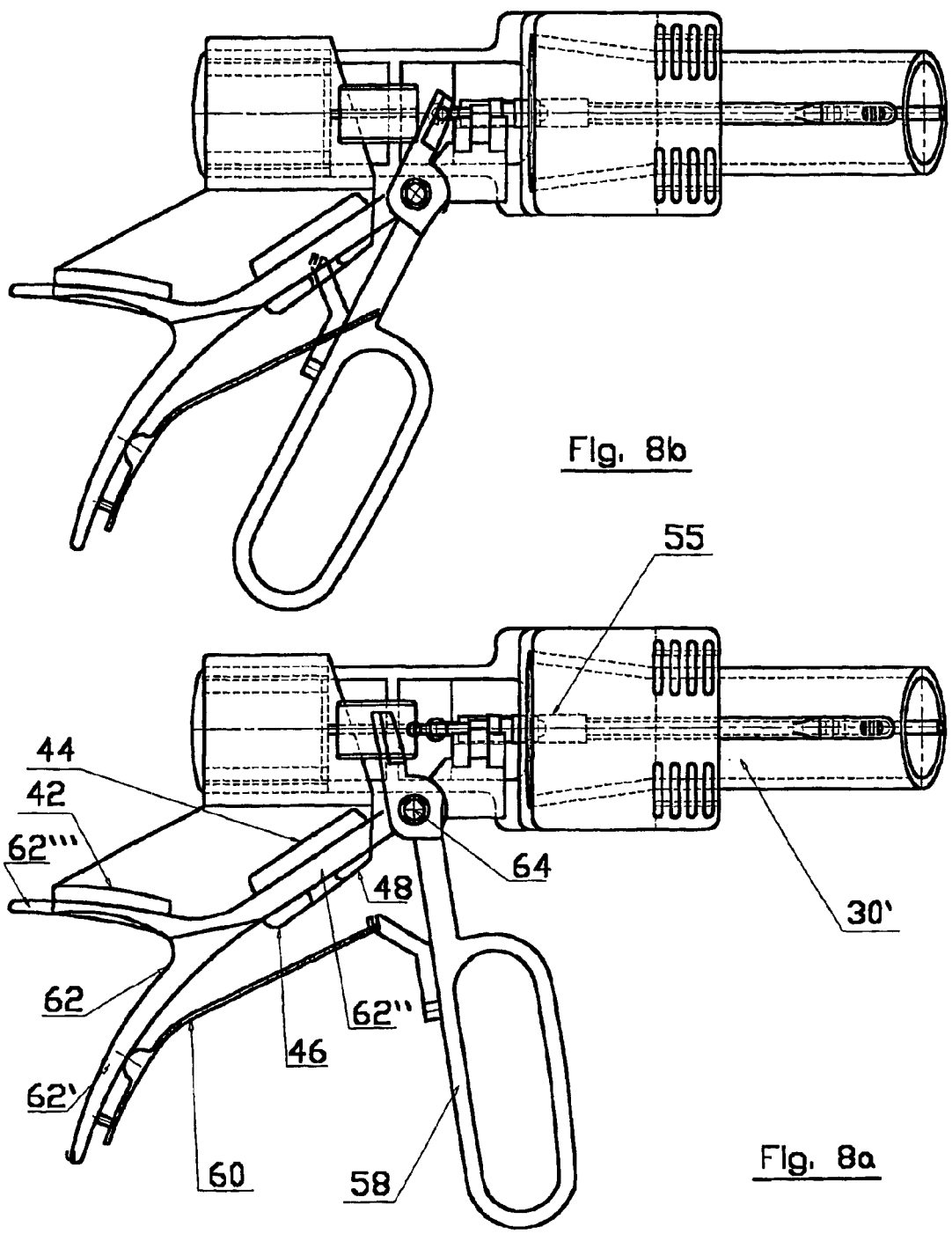

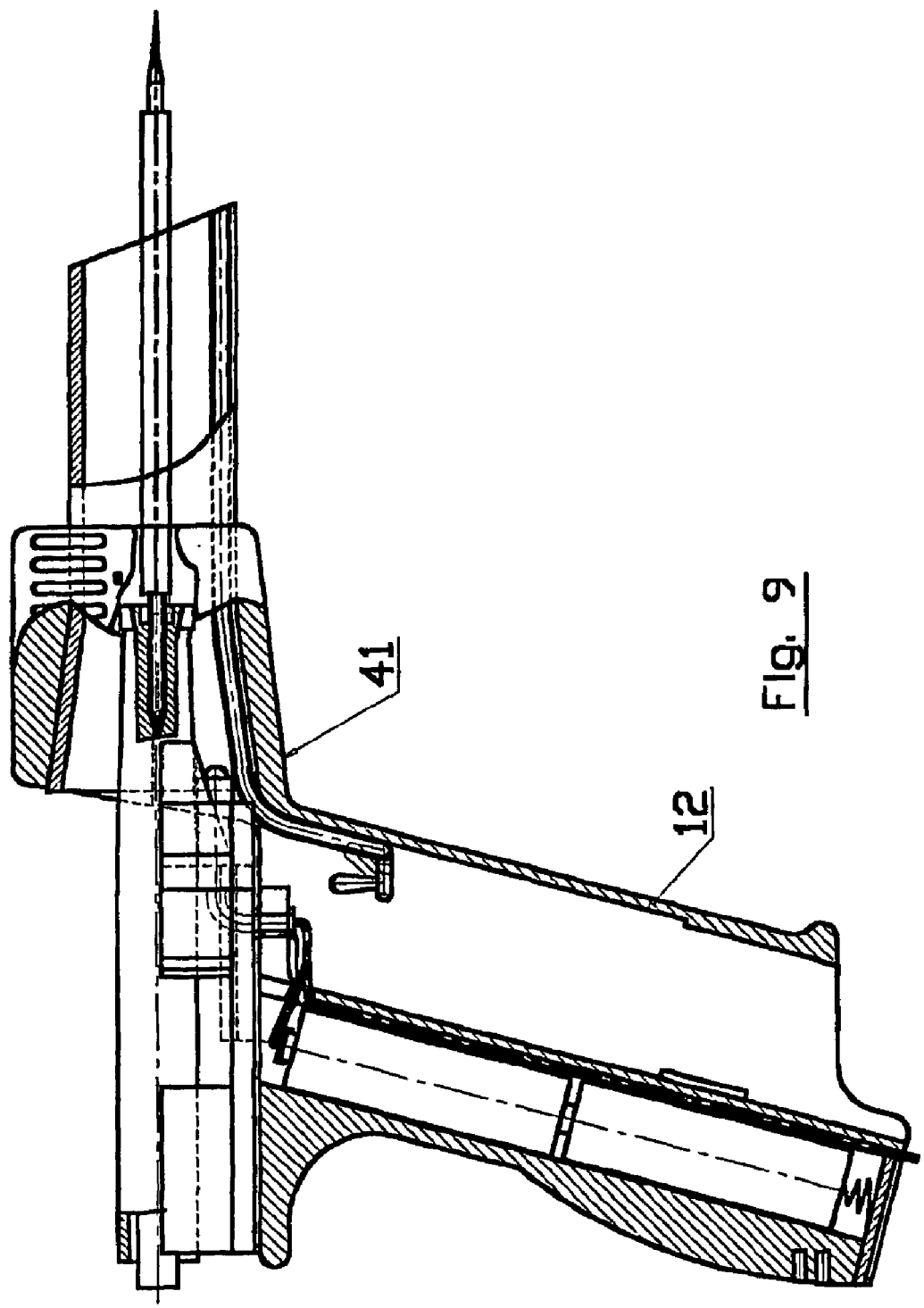

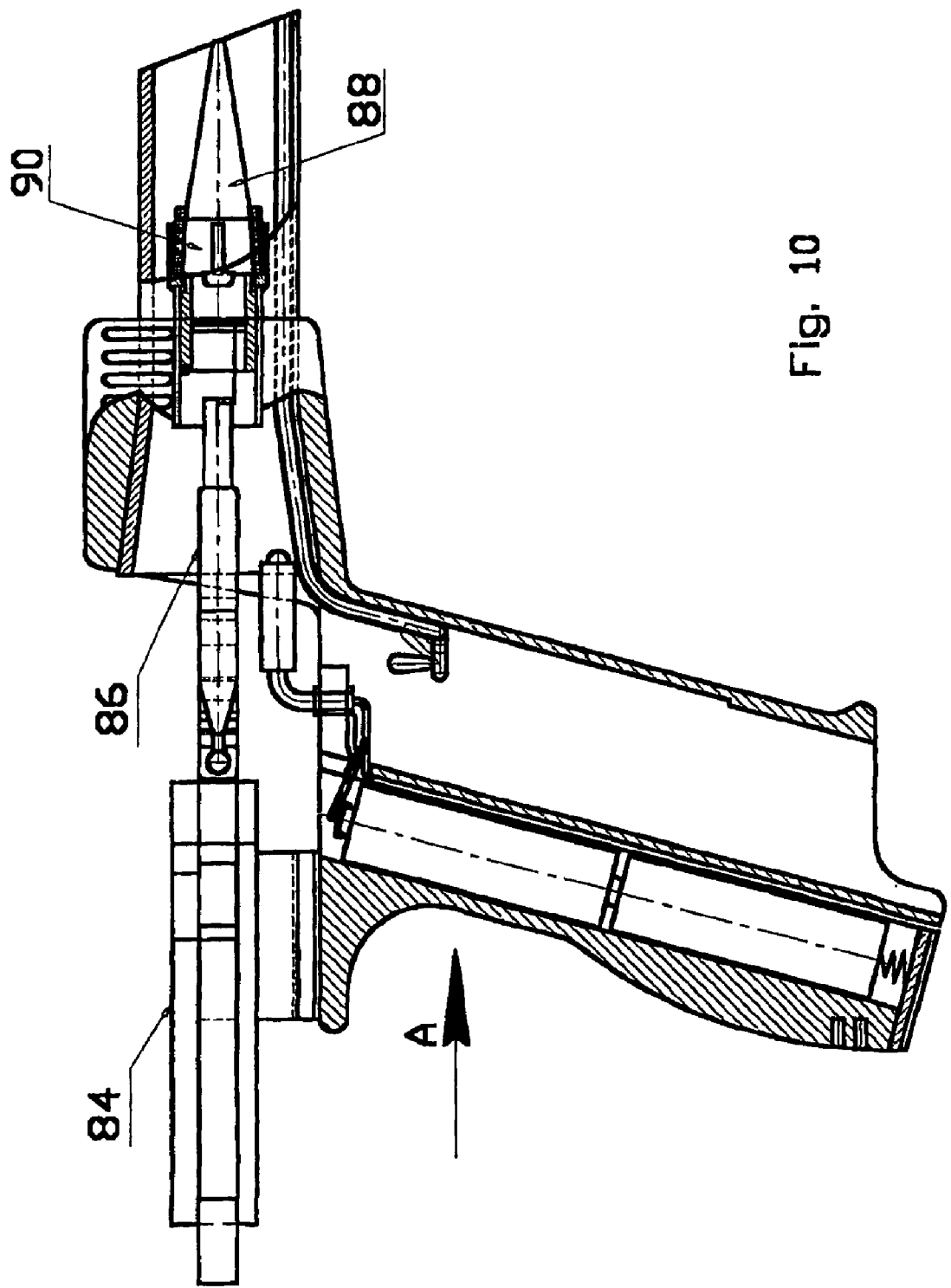

MULTIFUNCTIONAL MEDICAL TOOL

FIELD OF THE INVENTION

The present invention relates to a surgical tool, which can be used in various invasive proctologic treatments to be carried out in the anal canal, rectum or distal colon.

More particularly the invention refers to a surgical tool, which can be used during endoscopic examination of the above organs for prophylactics or for surgical treatments thereof, e.g. biopsy pathology examination, diathermia treatment, binding the hemorrhoids, or treatment of other rectal disorders.

It should be understood, however, that the present invention is not limited to the above treatments and it can be employed during other surgical procedures. In particular, the invention can be employed in surgical procedures which require manipulating a surgical instrument inserted within the anal canal.

BACKGROUND OF THE INVENTION

Various surgical instruments are known that require manipulation in the anal canal, e.g. anoscopes sigmoidoscopes, forceps, hemorrhoid ligators, etc.

Unfortunately, the prior art instruments are not convenient in use, since at least three hands are required to manipulate them and therefore they necessitate the presence of an assistant, which should operate in a coordinated manner with the surgeon. It can be readily appreciated that this complicates the medical procedure and renders it less efficient. Furthermore, since the instrument is not supported, the position thereof is not spatially determined and therefore it should be manipulated with very extra care, which renders the procedure inconvenient and tiresome.

There are known attempts to overcome the above problems.

For example, U.S. Pat. No. 5,158,563 discloses a single-operator hemorrhoid ligator, comprising a forceps, an endoscope with a fixedly attached track, an obturator, receivable within the endoscope and a loading mandrel, allowing an elastic ring to be mounted on the ligator. By virtue of combination of three instruments (ligator, forceps and endoscope) in one and by virtue of the fact that forceps and ligator are self-retained within the endoscope and supported by the track, the ligation procedure can be performed by a single operator, thus eliminating the necessity for assistance.

Unfortunately, this device is devised solely for ligation purposes and it is not intended for the other surgical procedures, which might be required during rectal treatment and which employ other surgical instruments.

Furthermore, the construction of the loading mandrel of this ligator enables loading of only single rubber ring and therefore it is required to reload the instrument after each ligation.

It can be readily appreciated, that the necessity in reloading of the ligator renders the whole ligation procedure time consuming.

In U.S. Pat. No. 5,464,412 is described a surgical instrument for elastic ring ligation of hemorrhoids by a solo operator. The instrument is formed as double-barreled endoscope, consisting of an exterior barrel and an interior barrel receivable within the external barrel. The operator inserts the tool into a body orifice by his one hand. The distal end of the interior barrel is loaded with a ring by means of a loading mandrel and the instrument is placed in the orifice aided by an obturator. The obturator is removed and the instrument is positioned to bring the target area into view. The selected tissue is drawn into the interior barrel, which functions as ligator. The operator can now pull the trigger on proximal end of the interior barrel, which retracts the barrel and releases elastic ring to be released by the exterior barrel.

This tool is also limited strictly to ligation of hemorrhoids and is not capable of carrying any other instruments required for other types of treatment.

There are known also in the art endoscopic tools in which by exchange of the surgical instrument it is possible to perform different treatments without necessity to introduce additional tool in the operation field.

An example of such multifunctional endoscopic surgical tool is disclosed in U.S. Pat. No. 5,186,714. This tool has been devised for laparoscopic surgery and it is suitable for several applications, e.g. percutaneous surgery, cholecystectomy, gynecology, neurosurgery and urology.

The tool is configured as a pistol-grip holder on which a tube or trocar with an interchangeable surgical instrument is mounted. The tool also comprises a cartridge, which is removably mounted on the holder and incorporates valves and tubes for connection to a source of vacuum and a source of flushing fluid. By virtue of this construction the tool can be used for many operations, like irrigation or suction of physiological matter, suction of gas or vapors, electrocautery, laparoscopy or laser surgery.

Unfortunately this multifunctional tool is limited strictly to laparoscopic surgery and it is not suitable for mounting of instruments, which usually are required for carrying out proctologic endoscopic operations within the anal canal.

It should be emphasized that despite the fact that different surgical devices for proctologic and other applications have been devised there still exists a need for a new and improved device which will ensure easy and convenient manipulation by different instruments during surgical treatment within the anal canal.

OBJECT OF THE INVENTION

The object of the present invention is to provide a new and improved proctologic surgical tool that reduces or overcomes the above-mentioned drawbacks of the known in the art surgical tools.

In particular, the main object of the present invention is to provide a new and improved surgical tool enabling efficient, convenient and reliable manipulation of the surgical instrument within the anal canal by two surgeon's hands without necessity of a third hand.

The further object of the present invention is to provide a new and versatile proctologic tool, enabling easy and fast replacement of the surgical instrument so as to carry out different treatments within the anal canal without necessity to withdraw the whole tool therefrom.

The third object of the present invention is to provide a new and improved proctologic tool, which is suitable, both for prophylactics, for endoscopic surgery and for any other type of surgical treatment, carried out within the anal canal, e.g. irrigation, flushing, suction, etc.

Still further object of the invention is to provide a new and improved proctologic tool, which enables performing ligation procedure without necessity in frequent reloading of ligation rubber rings.

The above and other objects and advantages of the present invention can be achieved in accordance with the following combination of its essential features, referring to different embodiments thereof.

In accordance with the main embodiment of the invention it constitutes a multifunctional medical tool substantially for use in proctologic applications, during which the surgeon has to manipulate a surgical instrument, brought within the anal canal. The tool of the invention comprises:
  a) a pistol-grip configured holder, adapted to carry the surgical instrument
  b) an endoscopic means, e.g. tubular cannula, which is detachably connected to the holder and is insertable within the anal canal and
  c) the surgical instrument, which can be brought in the anal canal through the tubular cannula,
  wherein said holder is provided with a lower handle portion to be held by the surgeon's one hand and with an upper lodgment portion adapted for securing the cannula and for supporting the surgical instrument so as to enable its convenient manipulation within the anal canal by the surgeon's second hand.

According to a further embodiment, said lodgment portion is defined by a front extremity and by a rear extremity, said front extremity is adapted to removably receive the cannula therein and said rear extremity is detachably connectable to a support member, and said support member is adapted to abut the surgical instrument.

In yet another embodiment, said handle portion is provided with a duct, which is in fluid communication with a source of flushing fluid, or compressed air, or vacuum, said handle portion is provided with a selector valve for connecting the duct either to the source of flushing fluid or to the source of compressed air or to the source of vacuum, said duct is capable to supply said flushing fluid, or compressed air, or vacuum through the tubular cannula within the anal canal.

In the further embodiment, said pistol-grip holder is provided with an illumination means, which is electrically connected with a source of energy, said illumination means is capable to project light through the tubular cannula within the anal canal.

In the additional embodiment the front extremity of the lodgment portion is provided with semicircle cross section, said front extremity is detachably connectable to an arcuate collar member, said front portion and said collar member define a through-going bore, suitable for insertion said cannula thereinto, said collar member is provided with spring-biased dovetail fasteners, adapted to co-operate with respective dovetail surfaces formed on the front extremity of the lodgment portion.

According to the further embodiment, said through-going bore is provided with conical interior adapted to secure the cannula tightly therein.

In still further embodiment, said support member is provided with at least one abutment location for placing thereon the surgical tool and with spring-biased dovetail fasteners, adapted to co-operate with respective dovetail surfaces formed on the rear extremity of the lodgment portion.

In yet another embodiment, said collar member is provided with an opening for insertion therethrough of an injection needle.

In the further embodiment, at least a portion of the outwardly facing surface of the collar member is corrugated to provide a better grip.

In accordance with the other embodiment, said surgical instrument is selected from the group consisting of a rubber band ligator, a biopsy forceps and a diathermia cutter.

In the further embodiment, said surgical instrument is provided with a scissor mechanism and said abutment location of the support member comprises a shelf, which laterally protrudes from the support member and is adapted to detachably receive the scissor mechanism.

And in still further embodiment, said abutment location comprises a rest means, protruding upwardly from the support member and adapted to support the instrument.

The present invention in its various embodiments has only been summarized briefly.

For better understanding of the present invention as well of its advantages, reference will now be made to the following description of its embodiments with reference to the accompanying drawings.

BRIEF DESCRIPTION OF THE DRAWINGS

FIGS. 1a,b and c are respectively a cross-sectional side view, a rear and a top view of the pistol-grip holder.

FIGS. 2a, b, c are respectively a partially cross-sectional side view, a front and a top view of the collar member.

FIG. 3 is a cross-sectional side view of the holder with the collar member mounted thereon.

FIGS. 4a and b are cross-sectional views of the cannula.

FIG. 5 is a cross-sectional side view of the holder with the cannula affixed thereto.

FIGS. 6a, b and c are respectively a side, a rear and a top view of the support member.

FIGS. 7a, b are respectively a side cross-sectional view and a rear view of the tool provided with biopsy forceps, provided with scissor mechanism.

FIGS. 8a, b show the biopsy forceps respectively in most retracted and most protracted position.

FIG. 9 is a side cross-sectional view of the tool provided with diathermia instrument.

FIG. 10 is a cross-sectional side view of the tool provided with rubber band ligator.

DETAILED DESCRIPTION OF SPECIFIC EMBODIMENTS

Figure 11:
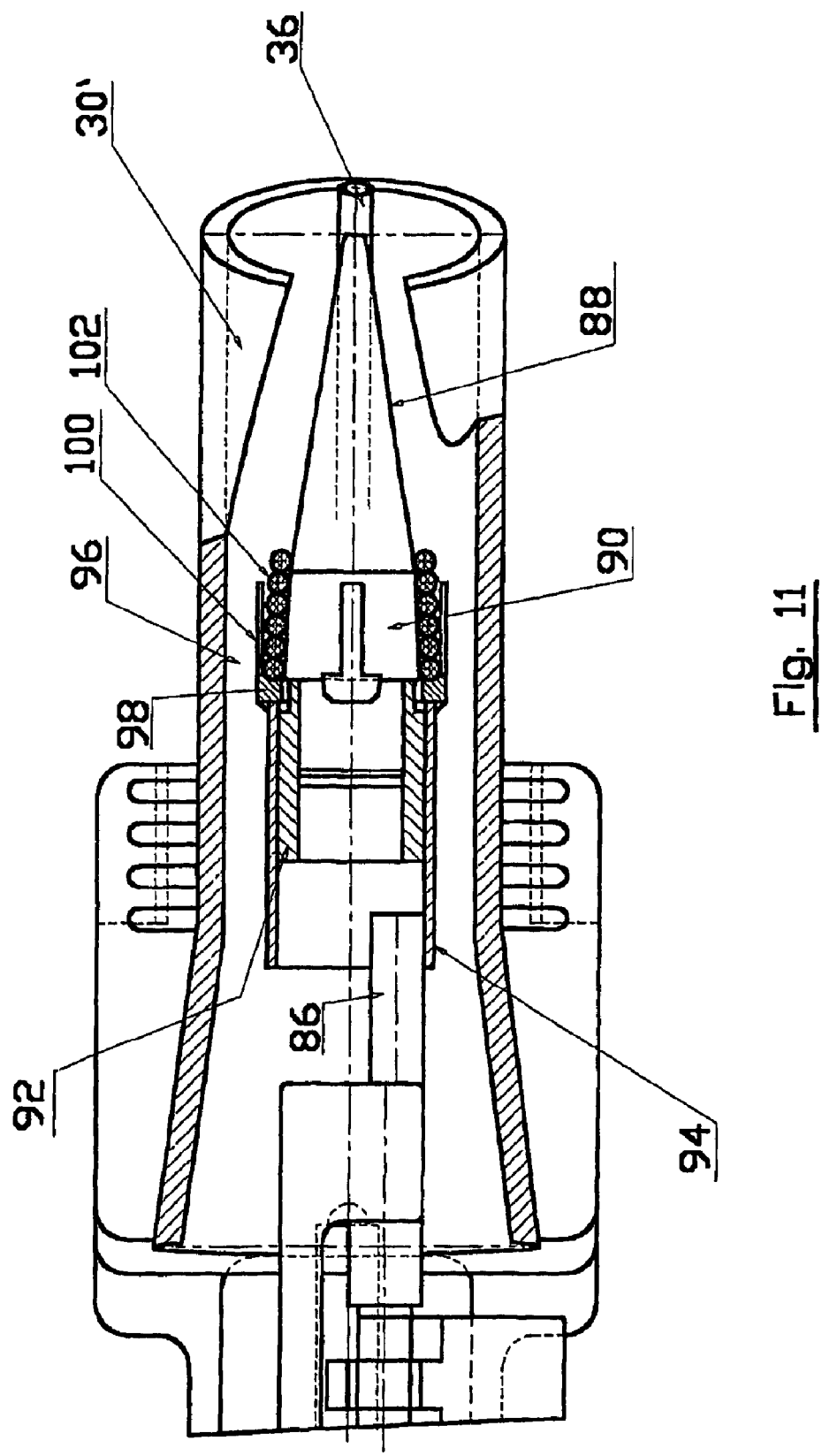
FIG. 11 is an enlarged cross-sectional view of the cannula and of the loading mandrel of the band ligator.

With reference to FIG. 1a, the tool of the invention comprises a holder 10, configured as pistol-grip body with a lower handle portion 12 and with an upper lodgment portion 14. The holder is made of appropriate, rigid plastic material from which it can be shaped, for example, by injection molding. The lodgment portion is intended for fastening thereon a tubular cannula or other suitable endoscopic means, and also for disposing a surgical instrument (not shown). In the beginning of treatment the surgeon grips the holder by one hand and inserts the cannula within the anal canal. Once the cannula is inserted, the surgeon puts the required instrument on the lodgment portion and brings it through the cannula within the anal canal and then manipulates it by the other hand in the course of treatment. As it will be explained further, the lodgment portion in accordance with the invention enables both easy and fast replacement of the instrument and at the same time reliable and convenient manipulation without external assistance of a nurse or other personal.

As seen in FIGS. 1a, b, the lodgment portion is defined by its front extremity 16, having semicircular cross-section and by a rear extremity 18.

It will be explained further with reference to FIGS. 2, 3 that on the front extremity a collar member is secured, which enables connecting the cannula with the tool. The upper ends of lateral sides of the front extremity are provided with dovetail depressions 16', 16" for connection with the corresponding dovetail connecting surfaces.

An elongated ramp 18' protrudes upwardly from the rear extremity of the lodgment portion. The ramp is provided with slanted lateral sides 18", 18''', which purpose will be explained further.

The handle portion of the holder is provided with two separate empty spaces 20 and 22. These empty space are intended for placing therein respectively of an autonomous source of energy (a battery) for energizing an illumination means and of a duct for supplying into the anal canal either a flushing fluid or a gas, or vacuum (not shown).

Mounted in the space 22 a sector valve 24 is provided, which connects the duct either to a source of flushing fluid or gas or vacuum. By virtue of the illumination means and the duct, the surgeon can visually inspect the anal canal through the cannula, and can also irrigate its interior, or perform suction or any other required action.

As best seen in FIGS. 2a, b, and c, the collar member is configured as an arch-bend body 26, suitable for securing on the front extremity 16. The lower part of the collar member is formed with dovetail connecting surfaces 26', 26", adapted to cooperate with respective dovetail depressions 16', 16" formed on the lateral sides of the front extremity. It can be easily appreciated that, by virtue of this provision, the collar member is secured on the front extremity once it is put thereon. The inwardly facing surface 28 of the collar member is configured as part of the truncated cone and the outwardly facing surface of the collar member is formed with shallow depressions 28' so as to provide a better grip.

At least one through-going bore 28" can be formed in the wall of the collar member for insertion therethrough of a needle (not shown), if this is required during the treatment.

Now with reference to FIG. 3 it is shown that, after the collar member has been secured on the front extremity of the lodgment portion, a tubular through-going opening 30 is formed between them. This opening is used for deployment of the cannula. The configuration of the opening is defined by the conical surface 28 of the collar member and by the inwardly facing surface of the front extremity. Since the forward end of the lodgment portion slightly ascends forward, its inwardly facing surface is also configured as truncated cone, similarly to surface 28 and thus the whole opening has the configuration of truncated cone.

An example of the endoscopic means, comprising a cannula is presented in FIGS. 4a, b. The cannula is configured as a tubular body 30', provided with a cylindrical front end 32, suitable for easy penetration within the anus and with a conical rear end 34, matching the configuration of the opening 30. Extending along the lower part of the cannula's interior an elongated groove 36 is provided for placement therein of the duct (not shown). The cannula is preferably made of plastic material so as to be disposable. It can be made also of stainless steel or other suitable metal and be used several times, providing it is disinfected after each use.

The size of the through-going bore and its cone angle is made slightly less than of the rear end of the cannula and, by virtue of this provision, the cannula can be tightly secured between the collar member and the lodgment portion of the holder. This situation is shown in FIG. 5.

Now with reference to FIGS. 6a, b and c, the construction of the support member, which is affixed to the rear extremity of the lodgment portion, will be explained.

The support member is configured as a flat substrate, provided with a central region 38 and a shelf 40, protruding laterally therefrom. A slightly bowed rest 41 protrudes upright from the forward end of the central region. The configuration and the size of the rest are chosen to reliably support the surgical instrument when it is put on the tool so as to assure its convenient manipulation by the surgeon's hand.

On the shelf are made upright partitions 42,44 and two small ledges 46,48, separated therebetween by a space 50. It will be explained further with reference to FIGS. 8a, b, that the configuration of the shelf portion as well the disposition of partitions and ledges is such that, if an instrument with a scissor mechanism is placed on the support member, the scissor mechanism is snapped between the partitions and ledges and is detachably affixed to the shelf portion. At the same time, the scissor mechanism is accessible to fingers of the surgeon's hand and he can conveniently operate the instrument.

Since the surgical instrument placed on the support member is always abutted both by the lateral shelf 40 or by the rest 41 its spatial position is better defined and this renders manipulation more convenient and efficient.

On the bottom of the support member are made dovetail-shaped connecting surfaces 52,54, which are configured to correspond to the slanted lateral sides 18", 18''' of the ramp 18'. By virtue of this provision the support member can be detachably affixed to the holder and the surgical instrument can be set up on it.

Now referring to FIGS. 7, 8 it is seen the tool of the invention, which is already assembled and the surgical instrument is placed on the support member. In this embodiment the instrument is conventional scissor-grip forceps, which is used for taking biopsy probe. This instrument consists of a scissor mechanism, operatively coupled with a working end 55, extending through the cannula towards the anal canal (not shown). A forceps 56 is mounted on the most forward extremity of the working end. The operation of this instrument is well known and therefore it will be explained here only briefly. The scissor mechanism consists of a ring-like pivotal handle 58, a flat spring 60 and a Y-shaped leg 62, consisting of branches 62', 62", 62'''. The spring is rigidly connected by its one end to branch 62' and by its opposite end to the handle, which can pivot about an axis 64. As seen in FIG. 8a, the branch 62" is snapped between the first partition 44 and ledges 46,48 of the shelf and the branch 62''' is laterally supported b the second partition 42. By virtue of this provision the whole leg is abutted by the shelf and is held steady thereon. When the surgeon does not hold the handle, the spring urges it to be in its most forward position, as shown in FIGS. 7a, 8a. In this position the handle brings the working end in retracted position, in which the forceps is open. When the surgeon, by fingers of his one hand brings the handle against the spring to the most rear position, as shown in FIG. 8b, the working end is brought to the most protracted position and the forceps is closed.

It can be readily appreciated that, by virtue of the above described lateral shelf, both the replacement and the setting up of any surgical instrument, employing conventional scissor-grip mechanism is simple and fast. At the same time, since the scissor mechanism is easily accessible it is convenient in operation.

As is also shown in FIG. 7a, a halogen bulb 65 is mounted under the rest 41 with the possibility of projecting light through the cannula towards the anal canal and thus to enable visual observation of its interior before or during the treatment. A wire 66 electrically connects the bulb with a couple of batteries 68,70, residing within the space 20 and energizing the bulb. Connected to the valve 24, a duct 72 extends along the groove 36 made in the cannula towards the anal canal.

Referring now to FIG. 9, another embodiment of the tool of the invention is shown, in which the tool carries a surgical instrument utilized for diathermia treatment.

The instrument consists of an elongated rear end 74, electrically connected by a couple of wires 76,78 to an external source of energy (not shown) and of a forward end 80, carrying a working tip 82. The rear end is readily accessible and during the treatment the surgeon holds and manipulates the instrument by his one hand, while his second hand grips the handle portion 12.

Since the rest 41 abuts the middle section of the instrument, the manipulation is more convenient and thus it is easier to bring the tip in contact with the required location in the anal canal.

Now with reference to FIGS. 10–12, a still further embodiment of the multifunctional tool of the invention is shown, in which the surgical instrument is a ligator for the binding of hemorrhoids.

In this embodiment, the surgical instrument includes the scissor mechanism 84 operatively connected through a pushing rod 86 to a loading assembly, bringing the elastic rubber rings towards the hemorrhoid. The scissor mechanism is similar to that shown in FIGS. 7, 8 in connection with the previously disclosed embodiment referring to biopsy forceps and thus shall not be described in detail here.

As best seen in FIG. 11, the loading assembly consists of a loading mandrel, formed with a forward conical elongated tip 88 and a rear conical loading segment 90, an internal centering bushing 92 and an external push bushing 94. A cup member 96 is provided, which is formed with a bottom portion 98 and a crown portion 100. The external bushing is mounted on the centering bushing with possibility for displacement therealong and is connected by its one end to the pushing rod 86 and by its opposite end to the bottom portion 98. By virtue of this provision, the external bushing and the cup member are displaceable together with the pushing rod.

The angle of the conical segment 90 is less steep than the tip 88 and the outside diameter D of the loading segment is less than the inner diameter of the crown portion. By virtue of this provision rubber rings can be placed in the annular space 102 between the crown and the loading segment along its length dimension L. These rings are loaded before the treatment and are arranged, as shown in FIG. 11 to be adjacent each other. It can be readily appreciated that annular space 102 has enough room to load more than one ring and in fact the length L of the loading segment defines the amount of rings.

The conical loading segment is also dimensioned to ensure that friction between the rings and the segment is sufficient to retain the rings stretched on the segment and to prevent them from being displaced off towards the tip. From the opposite direction the rings are prevented from displacing the segment by the bottom portion 98 of the cup member.

Figure 12B:
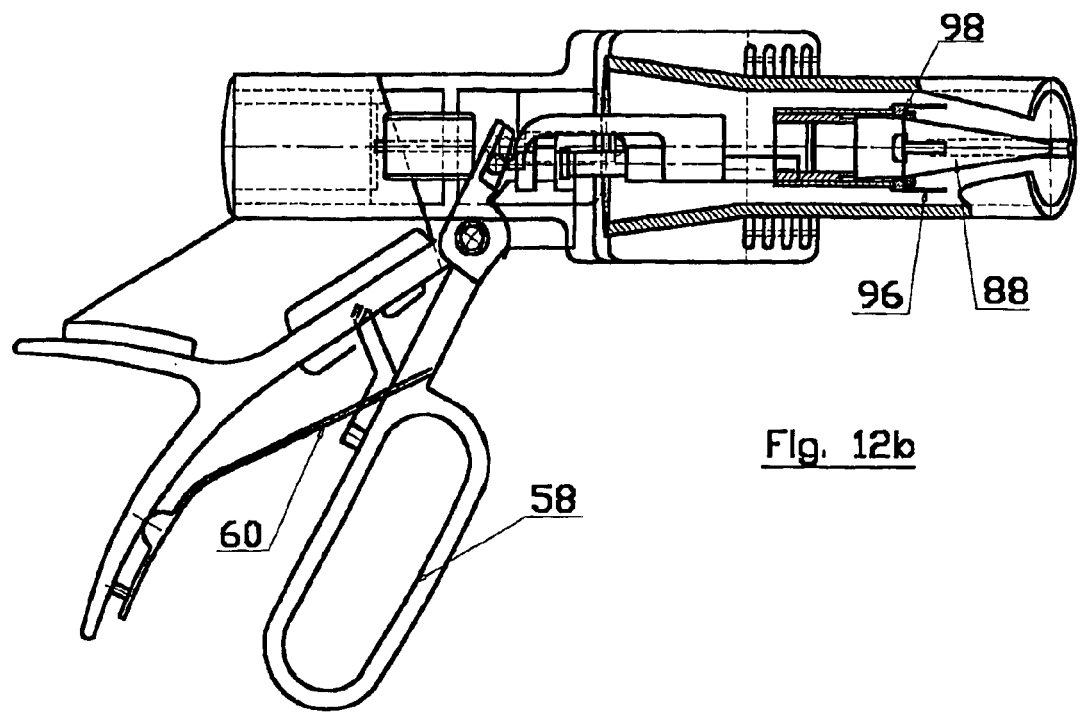
FIGS. 12a,b are show respectively most retracted and most protracted position of the band ligator.
Figure 12A:
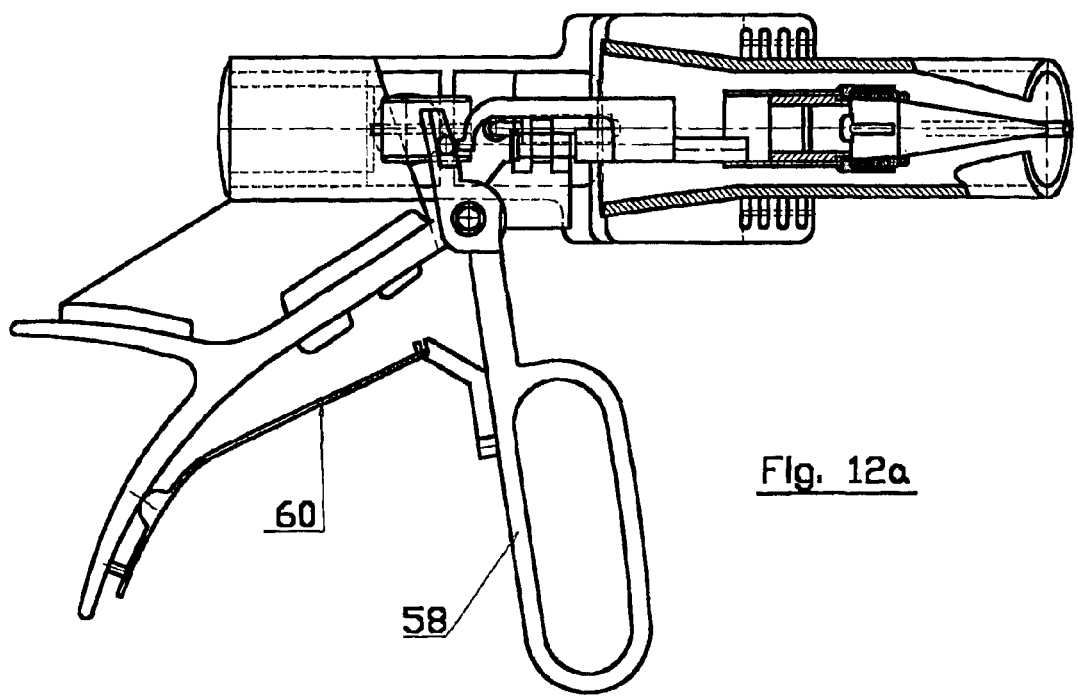

In the situation shown in FIGS. 10, 11, 12*a*, the handle 58 of the scissor mechanism is in its forward position, the pushing rod is retracted and the cup member does not urge the rings to displace away from the rear segment. The instrument is ready for ligation.

Once the scissor mechanism is brought in action and its handle 58 is displaced against spring 60 in the rear position, as shown in FIG. 12*b*, the pushing rod protracts forward together with the cup member 96. During this movement, the bottom portion 98 of the cup member urges the most forward rubber ring to displace off the segment 90 and it slides along the conical tip 88 towards the hemorrhoid to be ligated.

It can be realized that, by virtue of the above-described loading assembly, many rubber rings can be loaded and therefore there is no need in reloading of the instrument after each ligation.

As in the previous embodiment, associated with the forceps the scissor mechanism is reliably affixed to the support member and at the same time it is easily accessible.

The above-described tool enables convenient manipulation by any surgical instrument, which might be required during proctologic treatment, irrespective of whether the instrument is provided or not with the scissor mechanism. The tool does not require assistance of a nurse, since two surgeon hands can operate it.

Furthermore, the tool of the invention is multifunctional, since it allows fast and easy replacement of the instrument without removing the whole tool from the operation field.

It should be appreciated that the present invention is not limited to the above-described embodiments and that one ordinary skilled in the art can make modifications without deviation from the scope of the invention, as will be defined in the appended claims.

For example, the support member can be formed as an integral unit with the lodgment portion; the scissor mechanism can be affixed to the support member not by a snapping action, but by other mechanical means, instead of dovetail connecting surfaces one can use screws or other means.

It should also be appreciated that the features disclosed in the foregoing description, and/or in the following claims, and/or in the accompanying drawings may, both separately and in any combination thereof, be material for realizing the present invention in diverse forms thereof.

What is claimed is:

1. A multifunctional medical tool substantially for use in proctologic applications, during which surgeon has to manipulate a surgical instrument, brought within an anal canal, said tool comprising: a) a pistol-grip configured holder, adapted to carry the surgical instrument, b) an endoscopic means, which is detachably connected to the holder and is insertable within the anal canal, said endoscopic means having a tubular cannula, and c) the surgical instrument, which can be brought in the anal canal through the endoscopic means, wherein said holder is provided with a lower handle portion graspable by the surgeon's one hand and with an upper lodgment portion adapted for securing the endoscopic means thereon and for abutting the surgical instrument so as to enable its manipulation by the surgeon's second hand, said upper lodgment portion having a front extremity and a rear extremity, said front extremity adapted to removably receive the tubular cannula therein and said rear extremity detachably connected to a support member.

2. The multifunctional medical tool, as defined in claim 1, in which said handle portion is provided with a duct, which is in fluid communication with a source of flushing fluid, or a source of compressed air, or a source of vacuum, said handle portion is provided with a selector valve for connecting the duct either to the source of flushing fluid or to the source of compressed air or to the source of vacuum, said duct is capable to supply said flushing fluid, or compressed air, or vacuum through the endoscopic means within the anal canal.

3. The multifunctional tool, as defined in claim 1, in which said pistol-grip holder is provided with an illumination means, which is electrically connected to a source of energy, said illumination means is capable of projecting light through the endoscopic means within the anal canal.

4. The multifunctional tool, as defined in claim 1, in which said front extremity of the lodgment portion is provided with semicircle cross section, said front extremity is detachably connectable to an arcuate collar member, wherein said front portion and said collar member define through-going opening, which is suitable for insertion the cannula thereinto, said collar member is provided with dovetail connection surfaces, adapted to co-operate with respective dovetail connection surfaces formed on the front extremity of the lodgment portion.

5. The multifunctional tool as defined in claim 4, in which said through-going opening is provided with conical interior dimensioned to secure the cannula tightly therein.

6. The multifunctional tool as defined in claim 4, in which said support member is provided with at least one abutment location for abutting the surgical instrument and with dovetail connection surfaces, matching respective dovetail connection surfaces formed on the rear extremity of the lodgment portion.

7. The multifunctional tool as defined in claim 6, in which said surgical instrument selected from the group consisting of a rubber ring ligator, a forceps for taking biopsy probe and a diathermia cutter.

8. The multifunctional tool as defined in claim 7, in which said surgical instrument comprises rubber ring ligator, said ligator is provided with a scissor mechanism and a loading assembly adapted to put the rubber ring onto a hemorrhoid to be ligated.

9. The multifunctional tool as defined in claim 8, in which said loading assembly comprises a loading mandrel, comprising a forward conical tip directed towards the hemorrhoid and a rear conical segment, dimensioned to carry plurality of rubber rings, wherein the cone angle of said rear segment is steeper, than the cone angle of said tip.

10. The multifunctional tool as defined in claim 6, in which said surgical instrument is provided with a scissor mechanism.

11. The multifunctional tool as defined in claim 10, in which said abutment location comprises a shelf, extending laterally from the support member.

12. The multifunctional tool as defined in claim 11, in which said shelf is provided with a snap means, enabling to detachably connect the scissor mechanism to the support member.

13. The multifunctional tool as defined in claim 12, in which said scissor mechanism comprises a leg and said snap means comprises partitions and ledges, dimensioned to fix therebetween the said leg.

14. The multifunctional tool as defined in claim 6, in which said abutment location comprises a rest, protruding upwardly from the support member.

15. The multifunctional tool as defined in claim 4, in which said collar member is provided with at least one through-going bore for insertion therethrough of an injection needle.

16. The multifunctional tool as defined in claim 4, in which at least a portion of the outwardly facing surface of the collar member is corrugated to provide a better grip.

* * * * *